United States Patent [19]

Tam

[11] Patent Number: 4,538,003

[45] Date of Patent: Aug. 27, 1985

[54] MONOORGANYLATION OF DIHALOAROMATICS

[75] Inventor: Wilson Tam, Wilmington, Del.

[73] Assignee: E. I. Du Pont de Nemours and Company, Wilmington, Del.

[21] Appl. No.: 583,336

[22] Filed: Feb. 24, 1984

Related U.S. Application Data

[63] Continuation-in-part of Ser. No. 546,097, Oct. 27, 1983, abandoned.

[51] Int. Cl.$^3$ .................... C07C 41/18; C07C 17/00; C07C 25/02; C07C 25/18
[52] U.S. Cl. ................................ 568/656; 570/190; 568/634; 568/647
[58] Field of Search ............... 570/190; 568/634, 656, 568/647

[56] References Cited

PUBLICATIONS

Yamamura et al., Jour. Organometal. Chem 91 (1975), C39–C42.
Tamao et al., Bull. Chem. Soc. Japan 49 (1976), 1958–1969.
Minato et al., Tetrahedron Lett., 21 (1980) 845–848.
King et al., Inorg. Chem. 10 (1971), 1841–1850.
Corriu et al., JCS Chem. Comm., 144 (1972).
Tamao et al., J. Am. Chem. Soc., 94, pp. 4374 to 4376 (1972).
March, "Advanced Organic Chemistry", McGraw-Hill, NY, 1968, p. 509.
Coffey, Ed., "Rodd's Chemistry of Carbon Compounds", 2nd Edition, vol. IIIA, Elsevier, NY, 1971, pp. 241 to 287.
Negishi, Acc. Chem. Res., 15, 340 to 348 (1982) [Larson et al., Tetrahedron Lett., 5041 (1979)].
Eapen et al., J. Org. Chem., 1984, 49, 478 to 482.

*Primary Examiner*—Bernard Helfin
*Attorney, Agent, or Firm*—James A. Costello

[57] ABSTRACT

Process for the monoalkylation/monoarylation of dihaloaromatic compounds by treating the latter with selected magnesium or zinc organometallic reagents in the presence of a nickel/bidentate or tridentate phosphorus ligand. The products are intermediates to agricultural and pharmaceutical compounds.

50 Claims, No Drawings

MONOORGANYLATION OF DIHALOAROMATICS

CROSS-REFERENCE TO RELATED APPLICATION

This application is a continuation-in-part of copending application bearing U.S. Ser. No. 546,097 filed on Oct. 27, 1983 now abandoned.

BACKGROUND OF THE INVENTION

The process of this invention concerns the replacement of a halogen atom or an aromatic substrate by the alkyl or aryl moiety of a Grignard or zinc reagent. The reaction is catalyzed by a nickel/tridentate phosphorus catalyst complex, or a nickel/bidentate phosphorus catalyst complex in the presence of added triarylphosphine.

The selective cross-coupling of Grignard reagents with aryl halides is known: Corriu et al., *JCS Chem. Comm.*, 144 (1972); Tamao et al., *J. Am. Chem. Soc.*, 94, pages 4374 to 4376 (1972). In the latter publication, the reaction is catalyzed by a nickel-bidentate phosphine complex and the dihalo substrates give almost exclusively dialkyl products. A similar Grignard reaction: Yamamura et al., *J. Organometal. Chem.*, 91, C39 to C42 (1975), is catalyzed by a palladium-bidentate phosphine complex to give primarily dialkyl products.

Tamao et al., *Bull. Chem. Soc. Japan*, 49, pages 1958 to 1969, (1976) report that bidentate phosphine-nickel complexes give higher catalytic activity for the reaction of aryl halides with Grignard reagents. Dihaloaromatics are shown to ordinarily give dialkyl aromatic products. It is noted at page 1964 that "dichlorobenzenes are smoothly dialkylated even in the presence of two-fold excess of dichlorobenzene over the alkyl Grignard reagent". An Example at page 1963, Table 7, line 11, describes monoalkylation of a particular dihaloaromatic compound under reaction conditions different from those described herein.

Minato et al., in *Tetrahedron Lett.*, 21, pages 845 to 848 (1980), note that use of a palladium-monodentate or bidentate phosphine complex allows selective formation of monoalkylated products from dibromoaromatics.

Friedel-Crafts replacement reactions usually work poorly with dihalide-containing reactants and are often subject to alkyl rearrangement. In addition, halide replacement by an aryl substituent rarely works in Friedel-Crafts type reactions. Lithium alkylations and arylations of compounds containing dihalide substitution generally tend to give dialkylations and diarylations and are characterized by poor selectivities. See, in this regard, March, "Advanced Organic Chemistry", McGraw-Hill, N.Y., 1968, page 509. Other alkylation reactions are reviewed by Coffey, Ed., in "Rodd's Chemistry of Carbon Compounds", 2nd edition, Vol. IIIA, Elsevier, NY, 1971, pages 241 to 287.

Negishi, *Acc. Chem. Res.*, 15, 340 to 348 (1982) reviews the use of both Grignard and zinc reagents in selective crosscoupling reactions and notes the following arylzinc/aryl iodide reaction:

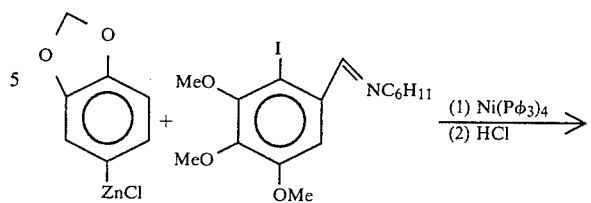

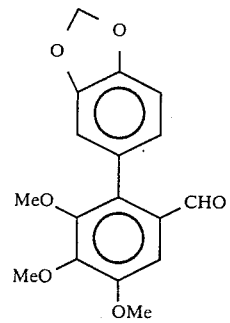

(Larson, et al., *Tetrahedron Lett.*, 5041 (1979)).

The characteristics by which the process of this invention differs from the various methods of the prior art as represented by the foregoing citations includes, in combination: selective formation of monoalkylated and-/or monoarylated products from dihaloaromatic starting reactants in good yield after relatively short reaction times employing easy to use nickel/bidentate or tridentate phosphorus complex catalysts. Certain of said catalysts are described by King et al., in *Inorg. Chem.*, 10, pages 1841 to 1850 (1971).

SUMMARY OF THE INVENTION

This invention concerns the monoorganylation of dihaloaromatic compounds comprising reacting a compound of the formula:

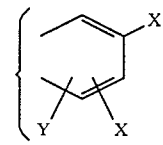

with RMX' in the presence of a nickel/bidentate or tridentate phosphorus catalyst complex to form:

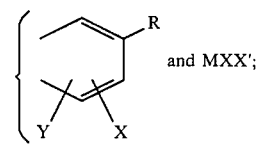 and MXX';

wherein

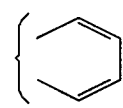

is an aromatic moiety selected from the group benzene, naphthalene, and anthracene;

X is individually Cl or Br, there being no more than one Br atom in the starting compound;

Y is hydrogen, $C_1$ to $C_{20}$ branched or straight chain alkyl or alkoxy, cycloalkyl, alkaryl, aryl, aralkyl; substituted alkyl, cycloalkyl, alkaryl, aryl, aralkyl, in which the substituents do not react with RMX';

R is $C_1$ to $C_{20}$ branched or straight chain alkyl containing no tertiary carbon centers bonded directly to M, cycloalkyl, alkaryl, aralkyl or aryl;

M is Mg or Zn; and

X' is Cl, Br or I;

when the catalyst is a nickel/bidentate phosphorus complex, at least one molar equivalent, based on nickel, of triarylphosphine is also present.

An excess of triarylphosphine of up to about 100 mols can be used to improve yields of monoorganylated products made employing the nickel/bidentate catalyst complex. Contemplated triarylphosphines include triphenylphosphine, tri(1-naphthyl)phosphine, and substituted triphenylphosphines such as tri(o-tolyl)phosphine, tri(m-tolyl)phosphine, tri(p-tolyl)phosphine and diphenyl-2-naphthylphosphine. Triphenylphosphine is preferred.

By "organylation" is meant the substitution of an alkyl or an aryl moiety for a chlorine or bromine substituent in an aromatic compound. Whether the substitution is by alkyl or aryl is determined of course by the organo moiety of the Grignard or zinc reagent.

Preferred values for Y are hydrogen or $C_1$ to $C_{20}$ branched or straight chain alkyl. Preferred values for R are $C_1$ to $C_{20}$ branched or straight chain alkyl containing no tertiary carbon centers bonded directly to M. Ni[triphosCl]PF$_6$ (triphos = [$\phi_2$P(CH$_2$)$\overline{2}$]$_2$P—$\phi$, where $\phi$ = C$_6$H$_5$) is the preferred catalyst because of its ease of synthesis and handling. Dichloroaromatics are preferred substrates because of their superior reactivity, o-dichloroaromatics being most preferred. Primary alkyl and aralkyl Grignard or zinc reagents are preferred because of superior selectivity and reactivity. Primary alkyl Grignard or zinc reagents are most preferred.

The reagents and catalyst are usually contacted with one another in a solvent at about 0°; the reaction occurs at about 25° C. to 70° C. Reaction in ether or THF at reflux conditions is the preferred manner of operation. The reaction is run under a relatively moisture-free inert gas atmosphere such as nitrogen, helium, argon, and the like.

The organometallic (Grignard or zinc) reagent is added at about 0.5 to 1.2 equivalents relative to the haloaromatic substrate in order to achieve the best monoorganylation selectivity. Catalyst concentrations typically range from about 0.01 mole percent to 10 mole percent.

DETAILS OF THE INVENTION

Table 1 below lists representative unsubstituted alkyl, alkoxy, cycloalkyl, alkaryl, aryl and aralkyl Y substituents.

TABLE 1

| Alkyl | | | | |
|---|---|---|---|---|
| Methyl | i-propyl | pentyl | t-pentyl | hexadecyl |
| ethyl | butyl | i-pentyl | hexyl | |
| propyl | t-butyl | neo-pentyl | dodecyl | |
| Cyclolalkyl | | | | |
| Cyclopropyl, -butyl, -pentyl, -hexyl, -heptyl, -octyl. | | | | |
| Alkaryl | | Aralkyl | | |
| tolyl | | benzyl | | |

TABLE 1-continued

| | |
|---|---|
| xylyl | phenethyl |
| mesityl | trityl |
| | diphenylmethyl |
| Aryl | Alkoxy |
| phenyl | methoxy |
| naphthyl | ethoxy |
| anthracenyl | |

Substituents that can be employed on the alkyl, alkoxy, cycloalkyl, alkaryl, aryl and aralkyl moieties represented in Table 1 are those that do not react with the Grignard or zinc reagent. Contemplated substituents include the alkyl, alkoxy, cycloalkyl and aryl groups recited in Table 1, as well as F, CF$_3$, and the like.

Representative R groups include those listed in Table 1 except for those in which a tertiary carbon is bonded directly to the metal (M).

The catalysts contemplated for use in the process of this invention are complexes of Ni with any of various bidentate or tridentate phosphorus ligands. Representative of the bidentate phosphorus ligands are:

(C$_6$H$_5$)$_2$P(CH$_2$)$_a$P(C$_6$H$_5$)$_2$, where a = 1, 2, 3 or 4;
(CH$_3$)$_2$P(CH$_2$)$_b$P(CH$_3$)$_2$, where b = 1, 2, 3 or 4; and
cis—(C$_6$H$_5$)$_2$PCH=CHP(C$_6$H$_5$)$_2$.

Representative of the tridentate phosphorus ligands are:

[(C$_6$H$_5$)$_2$P]$_3$CH,
[(C$_6$H$_5$)$_2$PCH$_2$]$_3$CCH$_3$,
[(C$_2$H$_5$)$_2$PCH$_2$]$_3$CCH$_3$,
[o—(C$_6$H$_5$)$_2$PC$_6$H$_4$]$_2$PC$_6$H$_5$,
[o—(C$_2$H$_5$)$_2$PC$_6$H$_4$]PC$_6$H$_5$,
C$_6$H$_5$P[(CH$_2$)$_2$P(cyclohexyl)$_2$]$_2$,
[(C$_6$H$_5$)$_2$P(CH$_2$)$_2$]$_2$PC$_6$H$_5$,
C$_6$H$_5$P[(CH$_2$)$_2$P(CH$_3$)$_2$]$_2$,
CH$_3$P[(CH$_2$)$_2$P(CH$_3$)$_2$]$_2$,
CH$_3$P[(CH$_2$)$_2$P(C$_6$H$_5$)$_2$]$_2$,
(CH$_3$)$_2$P(CH$_2$)$_2$P(C$_6$H$_5$)(CH$_2$)$_2$P(C$_6$H$_5$)$_2$,
(CH$_3$)$_3$CCH$_2$P[(CH$_2$)$_2$P(CH$_2$C(CH$_3$)$_3$)$_2$]$_2$,
and

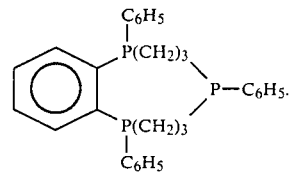

Anions that are useful in forming bidentate and tridentate phosphorus ligand catalysts include PF$_6^\theta$, Cl$^\theta$, Br$^\theta$, I$^\theta$, SbF$_6^\theta$, and BF$_4^\theta$.

The reaction is usually run in dry, coordinating ether solvents such as diethyl ether, ethyleneglycol dimethyl ether (glyme), diethyleneglycol dimethyl ether (diglyme), and tetrahydrofuran which do not react with Grignard or zinc reagents. Diethyl ether and tetrahydrofuran (THF) are preferred; a choice between the two depends upon solubility and temperature requirements of individual compounds.

For best results, methylmagnesium halides, benzylmagnesium halides and phenylmagnesium halides require, in addition to the catalyst, a separate activator for the catalyst. Another Grignard reagent (such as ethylmagnesium halide) or a borohydride (such as KBEt$_3$H) can be used for this purpose. The activator can be added to other magnesium halides and catalysts as necessary to improve yield. As a practical matter, if an activator is employed, no more is needed than about 1 equivalent per equivalent of catalyst.

It has been found that reaction of substrates with electron-donating substituents (such as alkyl groups) on the ring which are meta to a 1,3-pair of halogens give predominantly diorganylation except in the presence of methylmagnesium halides as the Grignard reagent. See, in this regard, Examples 26 and 27 wherein the yield of monoorganylated product in Example 26 (employing methylmagnesium iodide) is significantly in excess of the yield of Example 27 in which no methylmagnesium halide was used.

Representative of the literature concerning utility of products made by the process of this invention as intermediates for agricultural and pharmaceutical compounds are the following: for 2-chloro-3-ethylanisole in ascaricidal compositions, Schrotter et al., *Pharmazie*, 30, H.3 (1975), pages 147 to 151 and for 2-chloro-2-ethylbenzene, o-chlorotoluene, 1-chloro-4-isopropylbenzene, and 1-chloro-4- butylbenzene as intermediates to analgesics (U.S. Pat. No. 4,243,608) and anti-inflammatories (U.S. Pat. No. 4,251,535).

EXAMPLES

These Examples illustrate the invention. Gas chromatograph Column A referred to in the Examples comprises 10% by weight of polyethylene glycol, $HOCH_2(CH_2OCH_2)_xCH_2OH$, wherein x is about 450 (Carbowax ® 20M) on finely divided silica gel (80/100 Supelcoport ®). Column B comprises 10% by weight of a methyl silicone (SP-2100) on finely divided silica gel (100/120 Supelcoport ®).

After GC analysis, the compounds made by the methods described in the Examples were isolated by treating with $NH_4Cl$ solution, extracting with ether, drying over $MgSO_4$ and filtering. After solvent removal, product separation was by chromatography or distillation.

These abbreviations are employed in the Examples: Et=Ethyl, Bu=Butyl, Ph=Phenyl, $dppp=(C_6H_5)_2P(CH_2)_3P(C_6H_5)_2$, and

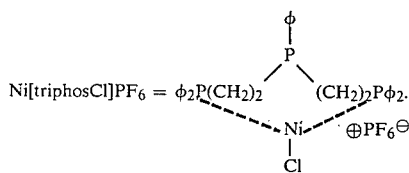

$Ni[triphosCl]PF_6 = \phi_2P(CH_2)_2 \quad (CH_2)_2P\phi_2$.

The latter compound (catalyst) was prepared by the method of King et al., *Inorg. Chem.*, 10, 1841 to 1850 (1971).

In Examples 3 and 4, respectively, EtMgBr and KBEt₃H were added to activate the catalyst. In Example 10, EtMgBr was added to activate the catalyst.

The general procedures followed in the Examples was to add the Grignard or zinc reagent to either a diethyl ether or THF solution containing the aryl halide and the nickel catalyst at 0° C. The mixture was refluxed or stirred at room temperature for a selected amount of time (usually overnight) and then analyzed by Gas Chromatography (GC) and/or GC/Mass Spec. (GC/MS).

EXAMPLE 1 o-Dichlorobenzene and EtMgBr

To 0.05 g (0.065 mmoles) of [NitrophosCl]PF₆ and 2.00 g (13.61 mmoles) of o-dichlorobenzene in 20 mL of ether at −78° C. was added 5.0 mL (14.50 mmoles) of 2.9M EtMgBr in ether. The mixture was warmed to room temperature and stirred for 5 days. GC on Column A indicated mainly starting dichlorobenzene. The mixture was refluxed overnight. GC on Column A indicated 1-chloro-2-ethylbenzene and diethylbenzene in the ratio of 4:1. This was confirmed by GC/MS. NH₄Cl solution was added and the mixture was extracted with ether. After drying over MgSO₄, the solvent was removed by rotary evaporation and the residue was flash-chromatographed on silica gel eluted with hexane. Thus obtained was 1.084 g (7.7 mmoles, 56.6%) of 1-chloro-2-ethylbenzene. ¹H NMR (200 MHz, CDCl₃): δ7.40 (m, 4H), 2.74 (q, J=7.6 Hz, 2H), 1.22 (t, J=7.6 Hz, 3H).

EXAMPLE 2 o-Dichlorobenzene and EtMgBr

The reaction of Example 1 was repeated except that the mixture was refluxed overnight after warming to room temperature. Then, 1.295 g of o-xylene was added as an internal NMR standard and the mixture was added to NH₄Cl solution. The mixture was extracted with ether, dried over MgSO₄, filtered, and the solvent was removed by rotary evaporation. ¹H NMR (200 MHz) in CDCl₃ indicated a 66% yield of 1-chloro-2-ethylbenzene and 20% of diethylbenzene.

EXAMPLE 3 o-Dichlorobenzene and EtMgBr/CH₃MgI

To 2.00 g (13.61 mmols) of o-dichlorobenzene, 0.05 g (0.065 mmoles) of [NiCltriphos]PF₆ in 5 mL of ether at −10° C. was added 0.3 mL (0.87 mmoles) of 2.9M EtMgBr in ether. The solution was stirred for 0.5 hr and then 20 mL of ether was added. The mixture was cooled to −78° C. and 5.0 mL (13.0 mmoles) of 2.6M CH₃MgI in ether was added. The reaction mixture was refluxed for 3 days; toluene was added as internal standard. GC analysis on Column A indicated 17% of o-xylene, 65% of 1-chloro-2-methylbenzene and 15% of o-dichlorobenzene.

EXAMPLE 4 o-Dichlorobenzene and CH₃MgI

The reaction of Example 3 was repeated except that 0.30 mL (0.3 mmoles) of 1M KBEt₃H in THF was used instead of EtMgBr. The reaction was worked up with NH₄Cl/ether and toluene was added to the concentrated ether extract. GC analysis on Column A indicated 45% of o-dichlorobenzene, 43% of 2-methyl-3-chlorobenzene and 10% of o-xylene.

EXAMPLE 5 o-Dichlorobenzene and nBuMgCl

To 0.05 g (0.065 mmoles) of [Ni Cltriphos]PF₆ and 2.00 g (13.61 mmoles) of o-dichlorobenzene in 20 mL of ether at −78° C. was added 7.0 mL (14.0 mmoles) of 2.0M n-butylMgCl in ether. After refluxing overnight, the sample was worked up to give 2.176 g of residue. To 0.047 g of the residue was added 0.030 g of o-xylene. ¹H NMR (200 MHz) spectrum in CDCl₃ indicated a total yield of 54% of 1-chloro-2-n-butylbenzene and 14% of o-dibutylbenzene.

EXAMPLE 6 o-Dichlorobenzene and n-DodecylMgBr

To 0.05 g (0.065 mmoles) of [NitriphosCl]PF$_6$ and 2.00 g (13.61 mmoles) of o-dichlorobenzene in 20 mL of ether at 0° C. was added 19.65 g (13.70 mmoles) of 0.697 mmoles/g of n-dodecylMgBr in THF. The mixture was refluxed overnight, poured into NH$_4$Cl solution, extracted with ether, dried over MgSO$_4$, and the solvent was removed by rotary evaporation. The residue was distilled (101° to 105° C./0.14 mm) to give 1.806 g (6.44 mmoles, 47.4%) of 1-chloro-2-dodecylbenzene. $^1$H NMR (200 MHz, CDCl$_3$): $\delta$7.4–7.0 (m, 4H), 2.70 (t, J=8 Hz, 2H), 1.6 (m, 2H), 1.3 (br s, 18H), 0.9 (m, 3H). High resolution mass spectrum: calculated for C$_{18}$H$_{29}$Cl: 280.1957; Found: 280.1954. Elemental analysis: Calculated for C$_{18}$H$_{29}$Cl: C, 76.97; H, 10.41; Found: C, 77.11; H, 10.47. IR(neat): 2935s, 2860s, 1478m, 1470m, 1460sh, 1445m cm$^{-1}$.

EXAMPLE 7

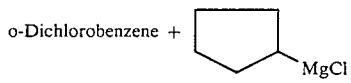

o-Dichlorobenzene +  ⬠-MgCl

To 2.00 g (13.61 mmoles) of o-dichlorobenzene and 0.05 g [NiCltriphos]PF$_6$ in 20 mL of THF at −78° C. was added 7.0 mL (14 mmoles) of 2M cyclopentylMgCl in ether. After refluxing for 2 days, the mixture was worked up with NH$_4$Cl solution. Then, 604 mg of the total residue (2.522 g total) was flash-chromatographed with 5% EtOAc/hexane. Thus obtained was 0.266 g of 1-cyclopentyl-2-chlorobenzene (representing a 45% yield of monoalkylated product). $^1$H NMR (200 MHz, CDCl$_3$): $\delta$7.2 (m, 4H), 3.43 (q, J=7.5 Hz, $^1$H), 2.05 (m, 2H), 1.6 (m, 6H). High resolution mass spectrum: calculated for C$_{11}$H$_{13}$Cl: 180.0705; Found: 180.0687.

EXAMPLE 8 o-Dichlorobenzene and BenzylMgCl

To 10.0 g (68.0 mmoles) of o-dichlorobenzene, 0.10 g (0.13 mmoles) of [NitriphosCl]PF$_6$ in 125 mL of ether at 0° C. was added 35 mL (70 mmoles) of 2M benzylMgCl in ether. The mixture was refluxed for 2 days. After the usual workup, the residue was distilled to give 1.616 g (11.0 mmoles, bp: 27° to 35° C./0.1 mm) of o-dichlorobenzene and 4.509 g (bp: 80° to 94° C./0.1 mm) of a clear liquid. The $^1$H NMR spectrum indicated this fraction to be a 6.9:1 mixture of 1-chloro-2-benzylbenzene and bibenzyl (19.7 mmole of 1-chloro-2- benzylbenzene and 2.86 mmole of bibenzyl). A 35% yield of 1-chloro-2-benzylbenzene based on reacted o-dichlorobenzene was obtained. $^1$H NMR (80 MHz, CDCl$_3$): 1-chloro-2-benzylbenzene: a singlet at $\delta$4.1 and aromatic H's at $\delta$7.2; bibenzyl: a singlet at $\delta$2.9 and aromatic H's at $\delta$7.2. GC/MS confirmed the presence of 1-chloro-2-benzylbenzene (M+ =202) and bibenzyl (M+ =182). The residue that did not distill over was chromatographed on silica gel eluted with 10% EtOAc/hexane to give 1.139 g (4.4 mmoles, 7% based on reacted o-dichlorobenzene) of 1,2-dibenzylbenzene.

EXAMPLE 9 o-Dichlorobenzene and BenzylMgCl

This Example illustrates the use of EtMgBr/[NitriphosCl]PF$_6$ as an activator/catalyst to improve yield. To 2.00 g (13.61 mmoles) of o-dichlorobenzene, 0.050 g (0.065 mmoles) of [NitriphosCl]PF$_6$ in 5 mL of ether at 0° C. was added 0.5 mL (1.5 mmoles) of 2.9M EtMgBr in ether. After stirring for 0.5 hrs, 30 mL of ether and 7.0 mL (14 mmoles) of 2M benzylMgCl in THF were added. The mixture was refluxed for 3 days and worked up as usual. After removing the solvent, the residue was distilled at 0.1 mm to initially remove 0.550 g (3.7 mmoles, 27%) of o-dichlorobenzene and then 1.482 g (bp: 68° to 83° C.) of a clear liquid was collected. $^1$H NMR spectrum in CDCl$_3$ indicated a 10:1 ratio of 1-chloro-2-benzylbenzene to bibenzyl (representing 6.7 mmoles (67% based on reacted o-dichlorobenzene) of 1-chloro-2-benzylbenzene and 0.67 mmoles of bibenzyl). The material that remained in the pot was chromatographed on silica gel eluted with 10% EtOAc/hexane to give 0.602 g (2.57 mmoles, 19%) of 1,2-dibenzylbenzene (mp: 61° to 67° C.).

EXAMPLE 10 o-Dichlorobenzene and PhMgBr

To 2.00 g (13.61 mmoles) of o-dichlorobenzene, 0.050 g (0.065 mmoles) of [NitriphosCl]PF$_6$ in 5 mL of ether at −10° C. was added 0.50 mL of 2.9M EtMgBr. After stirring for ½ hr, 25 mL of ether was added and the mixture was cooled to −78° C. Then, 6 mL of 2.3M (13.8 mmoles) PhMgBr was added. The solution was refluxed for 2 days. After the usual workup, 0.269 g of o-xylene was added and GC analysis on Column B indicated 2.55 mmoles of o-dichlorobenzene, 1.01 mmoles of biphenyl, 6.00 mmoles (53% based on reacted o-dichlorobenzene) of 1-chloro-2-phenylbenzene and 1.94 mmoles (17% based on reacted o-dichlorobenzene) of o-terphenyl all of which was confirmed by GC/MS.

EXAMPLE 11 o-Dichlorobenzene and isopropylMgCl

To 2.00 g (13.61 mmoles) of o-dichlorobenzene, 0.050 g (0.067 mmoles) of [NitriphosCl]PF$_6$ at 0° C. was added 5.2 mL (13.5 mmoles) of 2.6M isopropylMgCl in ether. The mixture was refluxed for 2 days. GC analysis on Column B indicated 0.6 mmole of chlorobenzene (6%), 3.7 mmoles of o-dichlorobenzene, 6.6 mmoles (67%) of 1-chloro-2-isopropylbenzene, 0.8 mmole (8%) of 1-chloro-2-propylbenzene, 0.9 mmole (9%) of 1,2-diisopropylbenzene and 0.4 mmole (4%) of 1-n-propyl-2-isopropylbenzene. Yields were based on reacted o-dichlorobenzene and were confirmed by GC/MS.

EXAMPLE 12 p-Dichlorobenzene and sec-butylMgCl

To 2.00 g (13.61 mmoles) of p-dichlorobenzene, 0.050 g (0.067 mmoles) of [NitriphosCl]PF$_6$ in 25 mL of THF at 0° C. was added 7.0 mL (14.0 mmoles) of 2M sec-butylMgCl in THF. After refluxing for 2 days, GC analysis on Column B indicated 20% of chlorobenzene, 23% of p-dichlorobenzene, 31% of 1-chloro, 4-sec-butylbenzene, 8% of 1-chloro-4-n-butylbenzene, 13% of 1,4-di-sec-butylbenzene and 4% of 1-sec-butyl-4-n- butylbenzene, which was confirmed by GC/MS. Yields are based on 13.61 mmoles of p-dichlorobenzene used.

EXAMPLE 13 o-Dichlorobenzene and sec-butylMgCl

Procedures were the same as those employed in Example 12 except that 2.00 g of o-dichlorobenzene was used. GC analysis on Column B indicated 9% of chlorobenzene, 26% of o-dichlorobenzene, 45% of 1-chloro-2-sec-butylbenzene, 6% of 1-chloro-2-n-butylbenzene, 5% of 1,2-di-sec-butylbenzene, and 3% of 1-n-butyl-2-sec-butylbenzene, all of which was confirmed by GC/MS.

EXAMPLE 14 m-Dichlorobenzene and sec-butylMgCl

Procedures were the sames as those employed in Example 12 except that m-dichlorobenzene was used. GC analysis on Column B indicated 30% of chlorobenzene, 28% of m-dichlorobenzene, 21% of m-chloro-3-n-butylbenzene, 11% of 1,3-di-sec-butylbenzene and 4% of 1-sec-butyl-3-n-butylbenzene, all of which was confirmed by GC/MS.

EXAMPLE 15 m-Dichlorobenzene and n-butyl Grignard

To 2.00 g (13.60 mmole) of m-dichlorobenzene, 0.050 g (0.065 mmoles) of [NitriphosCl]PF$_6$ in 20 mL of ether at −78° C. was added 7.0 mL (14.0 mmoles) of 2M nBuMgCl in ether. The mixture was refluxed for 2 hrs. Then, 0.841 g of o-xylene was added as an internal standard and GC analysis on Column A (70° C. (0 min), 16°/min to 220° C.) yielded 68% of 1-chloro, 3-n-butylbenzene and 23% of 1,3-di-n-butylbenzene which was confirmed by GC/MS.

EXAMPLE 16

1,4-Dichlorobenzene and EtMgBr

To 2.00 g (13.61 mmoles) of 1,4-dichlorobenzene and 0.050 g (0.065 mmoles) of [NiCltriphos]PF$_6$ in 25 mL of THF at −78° C. was added 5.0 mL (14.5 mmoles) of 2.9M EtMgBr in ether. The mixture was refluxed for 2 days. GC analysis indicated 71% of 1-chloro 4-ethylbenzene, and 11% of 1,4-diethylbenzene which was confirmed by GC/MS.

EXAMPLE 17

1,4-Dichlorobenzene and nBuMgCl

To 2.00 g (13.61 mmoles) of p-dichlorobenzene, and 0.050 g of [NiCltriphos]PF$_6$ in 20 mL of ether at −78° C. was added 7.0 mL (14 mmoles) of 2M nBuMgCl in ether. After refluxing overnight and workup with NH$_4$Cl solution, the residue (602 mg of 1.698 g) was flash-chromatographed with 5% EtOAc/hexane on silica gel to give 542 mg (67%) of 1-butyl-4-chlorobenzene. $^1$H NMR (200 MHz, CDCl$_3$): δ7.22 (m,2H), 7.05 (m,2H), 2.59 (t, J=5.5 Hz, 2H), 1.58 (m, 2H), 1.34 (m,2H) 0.95 (t, J=5.2 Hz, 3H). IR(neat): 2958s, 2930s, 2859s, 1492s, 1466m, 1407m, 1901s, 1016s cm$^{-1}$.

EXAMPLE 18

3,4-Dichlorotoluene and Ethyl Grignard

In a Schlenk flask was added 2.00 g (12.42 mmoles) of 3,4-dichlorotoluene, 0.050 g (0.065 mmoles) of [NitriphosCl]PF$_6$ in 20 mL of ether. The mixture was cooled to −78° C. and 4.5 mL (13.05 mmoles) of 2.9M EtMgBr in ether was added. The mixture was refluxed overnight. After the usual workup, the residue was flash-chromatographed on silica gel eluted with hexane. Three fractions were obtained: (1) 0.161 g; (2) 1.189 g; (3) 0.131 g. Fraction (1) was found to be 3-ethyl-4-chlorotoluene; $^1$H (200 MHz, CDCl$_3$): δ7.18 (d, J=8 Hz, 1H), 7.0 (s, 1H), 6.88 (d, J=8 Hz, 1H), 2.69 (q, J=7.5 Hz, 2H), 2.27 (s, 3H), 1.20 (t, J=7.5 Hz, 3H). Fraction (2) by GC on Column A (70° C. (0 min), 16° C./min to 220° C.) was indicated to be a mixture containing 20% of (3), 70% of (1) and 10% of starting dichlorotoluene. Fraction (3) was found to be 3,4-diethyltoluene; $^1$H NMR (CDCl$_3$, 200 MHz): δ7.0 (m, 3H), 2.60 (q, J=7 Hz, 4H), 2.29 (s, 3H), 1.20 (t, J=7 Hz, 3H), 1.19 (t, J=7 Hz, 3H). Total yields as calculated: 20% of (3), 52% of (1) and 6% of starting material.

EXAMPLE 19

2,5-Dichlorotoluene and CH$_3$MgI

To 2.00 g (12.42 mmoles) of 2,5-dichlorotoluene and 0.0500 g (0.065 mmols) of [NitrophosCl]PF$_6$ in 5 mL of ether at 0° C. was added 0.5 mL (1.5 mmoles) of 2.9M EtMgBr in ether. After 0.5 hrs at 0° C., 25 mL of ether and 5.0 mL (13.0 mmoles) of 2.6M CH$_3$MgI in ether were added. The mixture was refluxed overnight. After the usual workup, GC was run in a column comprising terephthalic acid derivative of Carbowax 20M (SP-1000) on silica gel (Chromosorb WAW) indicating 17% of 1,2,4-trimethylbenzene, 47% of 4-chloro-m-xylene, 30% of 4-chloro-o-xylene (retention time of authentic 4-chloro-o-xylene matches), and 3% of 2,5-dichlorotoluene, all of which was confirmed by GC/MS on 50–50 methyl-silicone capillary column.

EXAMPLE 20

2,3-Dichloroanisole and EtMgBr

To 0.05 g (0.065 mmoles) of [NiCltriphos]PF$_6$ and 2.00 g (11.30 mmoles) of 2,3-dichloroanisole in 20 ML of ether at −78° C. was added 4.0 mL (11.6 mmoles) of 2.9M EtMgBr. After refluxing overnight, the mixture was worked up in the usual way to give 1.875 g of residue. The residue was flash-chromatographed to give three fractions: (1) 0.252 g; (2) 1.223 g; (3) 0.155 g. Fraction (1) was chromatographed with 0.5% MeOH/Hexane to give 0.078 g of 2-ethyl-3-chloroanisole (0.46 mmoles, 4%). $^1$H NMR (200 MHz, CDCl$_3$): δ7.07 (t, J=8 Hz, 1H), 6.95 (d, J+8 Hz, 1H), 6.73 (d, J=8 Hz, 1H), 3.80 (s, 3H), 2.81 (q, J=7.5 Hz, 2H), 1.12 (t, J=7.5 Hz, 3H). Also, 0.113 g of 2-chloro-3-ethyl-anisole (0.66 mmoles, 5.9%) was obtained. Fraction (2) was determined to be 2-chloro-3-ethyl anisole (7.19 mmoles, 64%). $^1$H NMR (200 MHz, CDCl$_3$): δ7.14 (overlapping dd, J=8 Hz, 1H), 6.84 (d, J=8 Hz, 1H), 6.76 (d, J=8 Hz, 1H), 3.80 (s, 3H), 2.76 (q, J=7.5 Hz, 2H), 1.22 (t, J=7.5 H, 3H). High resolution mass spectra: Calculated for C$_9$H$_{11}$OCl: 170.0498; Found: 170.0477. IR(neat): 2978s, 2940s, 2880m, 2841m, 1600m, 1579s, 1475s, 1456m, 1438s, 1377w, 1330w, 1308w, 1308m, 1285s, 1266sh, 1116m, 1096s, 1090sh, 1060s, 1037m, 780s, 755m, 721m, 640m cm$^{-1}$. Elemental analysis calculated for C$_9$H$_{11}$OCl: C, 63.35; H, 6.50; Found: C, 63.52; H, 6.38. Fraction (3) was determined to be starting material (0.155 g, 7.7%).

EXAMPLE 21

2,6-Dichloroanisole and EtMgBr

To 2.00 g (11.30 mmoles) of 2,6-dichloroanisole, 0.05 g (0.067 mmoles) of [NitriphosCl]PF$_6$ in 25 mL of ether at 0° C. was added 4.0 mL (11.6 mmoles) of 2.9M EtMgBr in ether. After refluxing overnight, GC on a 50/50 methyl-silicone capillary column indicated 14% of 2,6-diethylanisole, 60% of 2-chloro-6-ethylanisole, and 20% of 2,6-dichloroanisole, all of which was confirmed by GC/MS. M+ of 164.10 (2,6-diethylanisole), 170.00 (2-chloro-6-ethylanisole) and 175.95 (2,6-dichloroanisole) were found.

EXAMPLE 22

2,4-Dichlorotoluene and EtMgBr

To 2.00 g (12.42 mmoles) of 2,4-dichlorotoluene, 0.050 [NitriphosCl]PF$_6$ in 35 mL of ether at 0° C. was added 4.3 mL (12.5 mmoles) of 2.9M EtMgBr in ether. After the reaction was refluxed overnight and worked-up as usual, the GC analysis in a 10% SP-1000 column indicated 57% of major isomer, 10% of minor isomer and 16% of 2,4-diethyltoluene. Preparative GC yielded pure components. The major isomer was determined to be 2-ethyl-4-chlorotoluene; $^1$H NMR (200 MHz, CD$_2$Cl$_2$): δ7.15 (m, 1H), 7.08 (m, 2H), 2.60 (q, J=7.5 Hz, 2H), 2.27 (s, 3H), 1.20 (t, J=7.5 Hz, 3H). The minor isomer was 4-ethyl-2-chlorotoluene.

EXAMPLE 23

2,4-Dichlorotoluene and CH$_3$MgI

To 2.00 g (12.42 mmoles of 2,4-dichlorotoluene, 0.050 g (0.065 mmoles) of [NitriphosCl]PF$_6$ in 5 mL of ether at 0° C. was added 0.50 mL (1.5 mmoles) of 2.9M EtMgBr in ether. After stirring for 0.5 hr, 25 mL of ether and 5.00 mL (13.00 mmoles) of 2.6M CH$_3$MgI were added. The mixture was refluxed overnight. GC analysis on 10% SP-1000 on chromosorb WAW indicated 44% of 4-chloro-o-xylene, 18% of 2-chloro-p-xylene and 28% of 1,2,4-trimethylbenzene.

EXAMPLE 24

2,6-Dichlorotoluene and n-ButylMgCl

To 2.00 g (12.42 mmoles) of 2,6-dichlorotoluene, 0.0500 g (0.065 mmoles) of [NitriphosCl]PF$_6$ in 35 mL of ether at 0° C. was added 6.20 mL (12.40 mmoles) of 2.0M n-butylMgCl in THF. After the mixture was refluxed overnight, a GC analysis on SP-1000 indicated 21% of starting dichloride, 49% of 2-chloro-6-n-butyltoluene and 30% of 2,6-di-n-butyltoluene which was confirmed by GC/MS.

EXAMPLE 25 o-Dichlorobenzene and EtZnCl

To 1.85 g (13.60 mmoles) of ZnCl$_2$ in 30 mL of THF was added 4.70 mL (13.63 mmoles) of 2.9M EtMgBr. After the mixture was stirred for 0.5 hrs, it was added dropwise to 2.00 (13.60 mmoles) of o-dichlorobenzene and 0.050 g (0.065 mmoles) of [NitriphosCl]PF$_6$ in 10 mL of THF. After the mixture was refluxed overnight, GC analysis on SP-1000 indicated 16% of o-diethylbenzene, 56% of 1-chloro-2-ethylbenzene and 28% of o-dichlorobenzene.

EXAMPLE 26

3,5-Dichlorotoluene and CH$_3$MgI

To 1.00 g (6.25 mmoles) of 3,5-dichlorotoluene and 0.050 g (0.065 mmoles) of [NitriphosCl]PF$_6$ in 5 mL of ether at −10° C. was added 0.5 mL (1.5 mmoles) of 2.9M EtMgBr. After the mixture was stirred for 0.5 hr, 25 mL of ether and 2.5 mL (6.5 mmoles) of 2.6M CH$_3$MgI in ether was added. After the mixture was refluxed overnight, GC analysis on SP-1000 indicated 10% of mesitylene and 57% of 3-methyl-5-chlorotoluene.

EXAMPLE 27

3,5-Dichlorotoluene and EtMgBr

To 0.800 g (4.97 mmoles) of 3,5-dichlorotoluene and 0.050 g (0.065 mmoles) of [NitriphosCl]PF$_6$ in 25 mL of ether was added 1.7 mL (4.9 mmoles) of 2.9M EtMgBr in ether. After the mixture was refluxed overnight, GC analysis on SP-1000 indicated 34% of 3,5-diethyltoluene, 21% of 3-chloro-5-ethyltoluene and 45% of starting dichloride, which was confirmed by GC/MS.

EXAMPLE 28

In a procedure analogous to that of Example 1, reaction of o-bromochlorobenzene with ethylmagnesium bromide in the presence of Ni[triphosCl]PF$_6$ would give principally monoalkylated products, for instance, o-bromoethylbenzene, and o-chloroethylbenzene and a lesser amount of the dialkylated product, o-diethylbenzene.

EXAMPLE 29 o-Dichlorobenzene and Methyl Magnesium Iodide

To 2.00 g (13.6 mmoles) of o-dichlorobenzene, 0.005 g (0.09 mmole) of Ni(dppp)Cl$_2$, and 0.10 g (0.38 mmole) of triphenylphosphine in 35 mL of ether was added 5.2 mL (13.5 mmoles) of 2.6 M methyl magnesium iodide in ether. The mixture was heated under reflux overnight, and the products were analyzed by G.C. on Column B. The analysis showed the presence of 33% of o-xylene, 38% of o-chlorotoluene, and 27% of unreacted o-dichlorobenzene.

In a control experiment in which no triphenylphosphine was added, G.C. analysis showed the presence of 38% of o-xylene, 4% of o-chlorotoluene, and 54% of unreacted o-dichlorobenzene.

EXAMPLE 30 o-Dichlorobenzene and Methyl Magnesium Iodide

The reaction mixture of Example 29 was employed except that 2.0 g (7.6 mmoles) of triphenylphosphine was used. The mixture was heated under reflux for 48 hours. G.C. analysis showed the presence of 10% of o-xylene, 62% of o-chlorotoluene, and 28% of unreacted o-dichlorobenzene.

EXAMPLE 31 o-Dichlorobenzene and Ethyl Magnesium Bromide

To 2.00 g (13.6 mmoles) of o-dichlorobenzene, 0.05 g (0.09 mmole) of Ni(dppp)Cl$_2$, and 2.0 g (7.6 mmoles) of triphenylphosphine in 35 mL of ether was added 4.7 mL (13.6 mmoles) of 2.9 M ethyl magnesium bromide in ether. The mixture was heated under reflux for 3 days, and the products were analyzed by G.C. on Column A. The analysis showed the presence of 10% of ethylbenzene, 14% of chlorobenzene, 3% of o-diethylbenzene, 51% of 1-chloro-2-ethylbenzene, and 23% of unreacted o-dichlorobenzene.

I claim:

1. A method for making compounds of the formula:

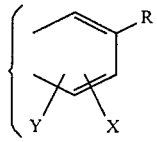

comprising reacting a compound of the formula:

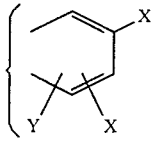

with the compound RMX'
wherein:

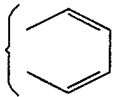

is an aromatic moiety selected from one of benzene, naphthalene or anthracene;

X is individually Cl or Br, there being no more than one Br atom in the starting compound;

Y is hydrogen, $C_1$ to $C_{20}$ branched or straight chain alkyl or alkoxy, cycloalkyl, alkaryl, aryl, aralkyl, substituted alkyl, cycloalkyl, alkaryl, aryl, aralkyl, in which the substituents do not react with RMX';

R is $C_1$ to $C_{20}$ branched or straight chain alkyl containing no tertiary carbon centers, cycloalkyl, alkaryl, aralkyl, or aryl;

M is Mg or Zn; and

X' is Cl, Br, or I;

in the presence of a nickel/bidentate phosphorus catalyst complex or a nickel/tridentate phosphorous catalyst complex; wherein the bidentate phosphorous ligands are selected from the group consisting of:

$(C_6H_5)_2P(CH_2)_aP(C_6H_5)_2$, where a = 1, 2, 3 or 4;
$(CH_3)_2P(CH_2)_bP(CH_3)_2$, where b = 1, 2, 3 or 4; and
cis-$(C_6H_5)_2PCH=CHP(C_6H_5)_2$;

and the tridentate ligands are selected from the group consisting of:

$[(C_6H_5)_2P]_3$, CH,
$[(C_6H_5)_2PCH_2]_3CCH_3$,
$[(C_2H_5)_2PCH_2]_3CCH_3$,
$[o\text{-}(C_6H)_5PC_6H_4]_2PC_6H_5$,
$[o\text{-}(C_2H_5)_2PC_6H_4]_2PC_6H_5$,
$\overline{C}_6H_5P[(CH_2)_2P(cyclohexyl)_2]_2$,
$[(C_6H_5)_2P(CH_2)_2]_2PC_6H_5$,
$C_6H_5P[(CH_2)_2P(CH_3)_2]_2$,
$CH_3P[(CH_2)_2P(CH_3)_2]_2$,
$CH_3P[(CH_2)_2P(C_6H_5)_2]_2$,
$(CH_3)_2P(CH_2)_2P(C_6H_5)(CH_2)_2P(C_6H_5)_2$,
$(CH_3)_3CCH_2P[(CH_2)_2P(CH_3C(CH_3)_3)_2]_2$, and

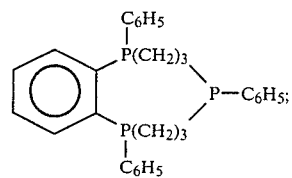

with the nickel/bidentate phosphorus catalyst complex, at least one molar equivalent, based on nickel, or triarylphosphine is also present during the reaction.

2. A method according to claim 1 wherein the catalyst is a nickel/tridentate phosphorus complex.

3. A method according to claim 1 wherein

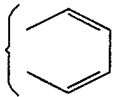

is benzene.

4. A method according to claim 1 wherein Y is selected from the group hydrogen or $C_1$ to $C_{20}$ branched or straight chain alkyl.

5. A method according to claim 3 wherein Y is selected from the group hydrogen or $C_1$ to $C_{20}$ branched or straight chain alkyl.

6. A method according to claim 1 wherein R is selected from the group $C_1$ to $C_{20}$ branched or straight chain alkyl containing no tertiary carbon centers bonded directly to the metal, M.

7. A method according to claim 3 wherein R is selected from the group $C_1$ to $C_{20}$ branched or straight chain alkyl containing no tertiary carbon centers bonded directly to the metal, M.

8. A method according to claim 7 wherein R is methyl, phenyl or benzyl.

9. A method according to claim 2 employing an activator for the catalyst complex.

10. A method according to claim 9 wherein the activator comprises a Grignard reagent or a borohydride.

11. A method according to claim 4 wherein R is selected from the group $C_1$ to $C_{20}$ branched or straight chain alkyl containing no tertiary carbon centers bonded directly to the metal, M.

12. A method according to claim 2 wherein the catalyst is Ni(triphosCl)PF$_6$.

13. A method according to claim 3 wherein the catalyst is Ni(triphosCl)PF$_6$.

14. A method according to claim 3 wherein each X is Cl.

15. A method according to claim 3 wherein one X is Cl and the other is Br.

16. A method according to claim 4 wherein each X is Cl.

17. A method according to claim 4 wherein one X is Cl and the other is Br.

18. A method according to claim 14 wherein Y is hydrogen or methyl.

19. A method according to claim 18 wherein Y is hydrogen and R is ethyl.

20. A method according to claim 18 wherein Y is hydrogen and R is butyl.

21. A method according to claim 18 wherein Y is hydrogen and R is dodecyl.

22. A method according to claim 18 wherein Y is hydrogen and R is cyclopentyl.

23. A method according to claim 18 wherein Y is hydrogen and R is benzyl.

24. A method according to claim 18 wherein Y is hydrogen and R is phenyl.

25. A method according to claim 18 wherein Y is hydrogen and R is isopropyl.

26. A method according to claim 18 wherein Y is hydrogen and R is sec-butyl.

27. A method according to claim 18 wherein Y is hydrogen and R is n-butyl.

28. A method according to claim 18 wherein Y is $CH_3$ and R is ethyl.

29. A method according to claim 18 wherein Y is $CH_3$ and R is n-butyl.

30. A method according to claim 18 wherein Y is $CH_3$ and R is methyl.

31. A method according to claim 7 wherein Y is methoxy and R is ethyl.

32. A method according to claim 1 wherein M is Mg.

33. A method according to claim 3 wherein M is Mg.

34. A method according to claim 5 wherein M is Mg.

35. A method according to claim 10 wherein M is Mg.

36. A method according to claim 11 wherein M is Mg.

37. A method according to claim 13 wherein M is Mg.

38. A method according to claim 14 wherein M is Mg.

39. A method according to claim 1 wherein M is Zn.

40. A method according to claim 3 wherein M is Zn.

41. A method according to claim 5 wherein M is Zn.

42. A method according to claim 10 wherein M is Zn.

43. A method according to claim 11 wherein M is Zn.

44. A method according to claim 13 wherein M is Zn.

45. A method according to claim 14 wherein M is Zn.

46. A method according to claim 1 wherein the catalyst is a nickel/bidentate phosphorus complex.

47. A method according to claim 46 wherein the bidentate phosphorus ligand is selected from the group consisting of $(C_6H_5)_2P(CH_2)_aP(C_6H_5)_2$, where $a=1, 2, 3$ or 4; $(CH_3)_2P(CH_2)_bP(CH_3)_2$, where $b=1, 2, 3,$ or 4; cis-$(C_6H_5)_2PCH=CHP(C_6H_5)_2$; and $[(C_6H_5)_2P]_2CH_2$.

48. A method according to claim 46 wherein the triarylphosphines are selected from the group consisting of triphenylphosphine, tri(1-naphthyl)phosphine, tri(o-tolyl)phosphine, tri(m-tolyl)phosphine, tri(p-tolyl)phosphine, and diphenyl-2-naphthylphosphine.

49. A method according to claim 47 wherein the triarylphosphines are selected from the group consisting of triphenylphosphine, tri(1-naphthyl)phosphine, tri(o-tolyl)phosphine, tri(m-tolyl)phosphine, tri(p-tolyl)phosphine and diphenyl-2-naphthylphosphine.

50. A method according to claim 49 wherein the triarylphosphine is triphenylphosphine.

* * * * *